US012765802B2

(12) United States Patent
Jameson et al.

(10) Patent No.: US 12,765,802 B2
(45) **Date of Patent: *Oct. 20, 2026**

(54) BREATH SENSOR CALIBRATION METHODS AND APPARATUS

(71) Applicant: Pivot Health Technologies Inc., San Carlos, CA (US)

(72) Inventors: Allen Jameson, Lake Oswego, OR (US); Brian Herold, San Mateo, CA (US); Eric Tridas, Sunnyvale, CA (US)

(73) Assignee: Pivot Health Technologies Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/536,904

(22) Filed: Dec. 12, 2023

(65) Prior Publication Data

US 2024/0108243 A1 Apr. 4, 2024

Related U.S. Application Data

(63) Continuation of application No. 17/132,551, filed on Dec. 23, 2020, now Pat. No. 11,957,451.

(Continued)

(51) Int. Cl.
*A61B 5/097* (2006.01)

(52) U.S. Cl.
CPC ...... *A61B 5/097* (2013.01); *A61B 2560/0223* (2013.01); *A61B 2562/0271* (2013.01); *A61B 2562/029* (2013.01)

(58) Field of Classification Search
None
See application file for complete search history.

(56) References Cited

U.S. PATENT DOCUMENTS

| | | | |
|---|---|---|---|
| 4,358,424 | A | 11/1982 | Weber et al. |
| 4,633,704 | A | 1/1987 | Tantram et al. |

(Continued)

FOREIGN PATENT DOCUMENTS

| | | |
|---|---|---|
| CA | 2736243 | 3/2010 |
| WO | WO 2010/005738 | 1/2010 |

(Continued)

OTHER PUBLICATIONS

Raiff et al., "Breath Carbon Monoxide Output is Affected by Speed of Emptying the Lungs: Implications for Laboratory and Smoking Cessation Research." Nicotime Tob Res., Jun. 7, 2010; 12(8):834-838.

*Primary Examiner* — Jason M Sims
*Assistant Examiner* — Matthew Eric Ogles
(74) *Attorney, Agent, or Firm* — Levine Bagade Han LLP

(57) ABSTRACT

Breath sensor calibration methods and apparatus are described herein where a breath sensor device may generally comprise a sampling unit having a housing configured to receive a sample breath from a user and a sensor positioned within the housing. A processor in electrical communication with the sensor may be configured to determine a dissipation time when the sensor is exposed to a near-constant concentration level of CO detected from the breath sample down to an ambient level of CO detected. The processor may also be configured to calculate a time constant based on the dissipation time and a reduction from the near-constant concentration level to the ambient level. Furthermore, the processor may also be configured to apply the time constant to a transient response of the sensor to account for drift in calibrating the sensor.

8 Claims, 7 Drawing Sheets

Related U.S. Application Data

(60) Provisional application No. 62/955,558, filed on Dec. 31, 2019.

(56) References Cited

U.S. PATENT DOCUMENTS

| | | | | |
|---|---|---|---|---|
| 5,404,885 | A | 4/1995 | Sheehan et al. | |
| 6,443,908 | B2 | 9/2002 | Stone | |
| 6,479,019 | B1 | 11/2002 | Goldstein et al. | |
| 6,733,463 | B2 | 5/2004 | Moilanen et al. | |
| 6,733,464 | B2 | 5/2004 | Olbrich et al. | |
| 6,840,084 | B2 | 1/2005 | Nikolskaya | |
| 7,204,335 | B2 | 4/2007 | Stewart et al. | |
| 8,266,795 | B2 | 9/2012 | Wagner | |
| 9,709,582 | B1 | 7/2017 | Gordon et al. | |
| 10,458,992 | B2 | 10/2019 | Silkaitis et al. | |
| 10,499,819 | B2 | 12/2019 | Wondka et al. | |
| 10,861,595 | B2 | 12/2020 | Satake et al. | |
| 10,923,220 | B2 | 2/2021 | Satake | |
| 11,209,417 | B2 | 12/2021 | Jameson et al. | |
| 11,796,532 | B2 | 10/2023 | Jameson et al. | |
| 11,957,451 | B2 * | 4/2024 | Jameson | A61B 5/097 |
| 2001/0049477 | A1 | 12/2001 | Stone | |
| 2003/0208133 | A1 | 11/2003 | Mault | |
| 2005/0083527 | A1 | 4/2005 | Flaherty et al. | |
| 2006/0266353 | A1 | 11/2006 | Yamada et al. | |
| 2007/0288266 | A1 | 12/2007 | Sysko et al. | |
| 2008/0114223 | A1 | 5/2008 | Pierry et al. | |
| 2009/0220948 | A1 | 9/2009 | Oviso et al. | |
| 2010/0268106 | A1 | 10/2010 | Johnson et al. | |
| 2011/0021940 | A1 | 1/2011 | Chu et al. | |
| 2012/0266654 | A1 | 10/2012 | Chiarugi et al. | |
| 2012/0310104 | A1 | 12/2012 | Van Kesteren et al. | |
| 2014/0275857 | A1 | 9/2014 | Toth et al. | |
| 2014/0316296 | A1 | 10/2014 | Meng et al. | |
| 2014/0358019 | A1 | 12/2014 | Johnson | |
| 2015/0105684 | A1 | 4/2015 | Yano et al. | |
| 2015/0164373 | A1 | 6/2015 | Davis et al. | |
| 2015/0201865 | A1 | 7/2015 | Forzani et al. | |
| 2015/0260706 | A1 | 9/2015 | Killard et al. | |
| 2015/0265184 | A1 | 9/2015 | Wondka et al. | |
| 2015/0347689 | A1 | 12/2015 | Neagle | |
| 2015/0362478 | A1 | 12/2015 | Phillips | |
| 2016/0033340 | A1 * | 2/2016 | Todd | G01K 15/005 374/1 |
| 2016/0073930 | A1 | 3/2016 | Stetter et al. | |
| 2016/0077086 | A1 | 3/2016 | Holmes et al. | |
| 2016/0084861 | A1 | 3/2016 | Kleider et al. | |
| 2016/0331272 | A1 | 11/2016 | Ahmad et al. | |
| 2017/0055875 | A1 | 3/2017 | Candell et al. | |
| 2017/0074844 | A1 | 3/2017 | Tolmie et al. | |
| 2017/0119279 | A1 * | 5/2017 | Ahmad | A61B 10/00 |
| 2017/0176411 | A1 | 6/2017 | Trainor et al. | |
| 2017/0191984 | A1 | 7/2017 | Ma | |
| 2017/0192008 | A1 | 7/2017 | Silkaitis et al. | |
| 2017/0265778 | A1 | 9/2017 | Reichlyn et al. | |
| 2017/0284999 | A1 * | 10/2017 | Maric | G01N 33/0037 |
| 2018/0271403 | A1 | 9/2018 | Furusaki et al. | |
| 2019/0017996 | A1 | 1/2019 | Chou et al. | |
| 2019/0113501 | A1 | 4/2019 | Jameson et al. | |
| 2019/0117138 | A1 | 4/2019 | Budiman et al. | |
| 2019/0261891 | A1 | 8/2019 | Ahmad et al. | |
| 2019/0339224 | A1 * | 11/2019 | Bhavaraju | A61B 5/14532 |
| 2019/0344281 | A1 | 11/2019 | Ahmad et al. | |
| 2020/0197580 | A1 | 6/2020 | Kilpadi et al. | |
| 2020/0305729 | A1 | 10/2020 | Wondka et al. | |
| 2021/0057066 | A1 | 2/2021 | Satake et al. | |
| 2021/0196148 | A1 | 7/2021 | Jameson et al. | |
| 2021/0204834 | A1 | 7/2021 | Jameson et al. | |
| 2021/0290101 | A1 | 9/2021 | Douglas | |
| 2022/0082550 | A1 | 3/2022 | Jameson et al. | |
| 2023/0417735 | A1 | 12/2023 | Jameson et al. | |

FOREIGN PATENT DOCUMENTS

| | | |
|---|---|---|
| WO | WO 2019/074666 | 4/2019 |
| WO | WO 2021/138195 | 7/2021 |
| WO | WO 2021/138197 | 7/2021 |

* cited by examiner

BREATH SENSOR CALIBRATION METHODS AND APPARATUS

CROSS-REFERENCE TO RELATED APPLICATIONS

This application is a continuation of U.S. patent application Ser. No. 17/132,551 filed Dec. 23, 2020, which claims the benefit of priority to U.S. Prov. App. 62/955,558 filed Dec. 31, 2019, each of which is incorporated herein by reference in its entirety.

FIELD OF THE INVENTION

The present invention relates to apparatus and methods for maintaining accuracy over time of devices which receive and detect biological parameters from breath samples. In particular, the present invention relates to apparatus and methods for calibrating breath sensors which naturally degrade over time.

BACKGROUND OF THE INVENTION

The health problems associated with tobacco smoking are well known. Cigarette smoke contains nicotine as well as many other chemical compounds and additives. Tobacco smoke exposes an individual to carbon monoxide (CO) as well as these other compounds, many of which are carcinogenic and toxic to the smoker and those around the smoker. The presence and level of CO in the exhaled breath of the smoker can provide a marker for identifying the overall smoking behavior of that individual as well as provide a marker for their overall exposure to the other toxic compounds.

In order to sample the exhaled breath, a portable breath sensor which is readily carried by the user and which is unobtrusive is desirable. However, the relatively reduced size of the breath sensor also brings a number of challenges in capturing and accurately measuring samples of the exhaled breath. Factors such as moisture content in the breath as well as breath temperature may affect the accuracy of the sensors used to measure the parameters due to the relatively small size.

In order to sample the exhaled breath, a portable breath sensor which is readily carried by the user and which is unobtrusive is desirable. While this portable breath sensor can measure the exhaled carbon monoxide (eCO) values of users, it may not be immediately intuitive to all users how to use this data since it may not be a widely understood metric.

Electrochemical sensors typically contained within portable breath sensors for detecting carbon monoxide levels from exhaled breath may degrade over time such that the sensor sensitivity degrades. This decrease in sensor sensitivity over time is typically consistent for such sensors provided that the sensors are kept away from environment extremes. The transient response of the sensor, however, can change on a per-device basis in a manner not necessarily predictable with the kind of sensor inputs available in the device.

Accordingly, there remains a need for methods and devices which are able to correct for the change in properties within the sensors and which allows for a longer useful life of the sensor and higher accuracy especially for short-duration exposures (e.g., short exhalation periods from the user).

SUMMARY OF THE INVENTION

From the time that a breath sampling device is manufactured to the time that the device is actually in use in the hands of a user, there is typically a period of time that the breath sampling device is stored prior to its use. During this period of time, the electrochemical sensors may begin to degrade such that the sensor sensitivity also degrades resulting in inaccurate sensor readings when put into use.

In order increase the useful life of the breath sensor for detecting analytes such as carbon monoxide (CO) from a user, various methods may be employed which increases the shelf life of the breath sampling device prior to being sold to the user and which also results in longer use by the user as well. This may not only increase the accuracy of the breath sensor but may also increase the ease-of-use of the sensor by providing a highly-accurate reading from breaths having relatively shorter exhalation durations than otherwise allowable.

Examples of breath sampling devices and methods for determining and quantifying eCO levels from a user are described in further detail in various patents, e.g., U.S. Pat. Nos. 9,861,126; 10,206,572; 10,306,922; 10,335,032, and U.S. Pat. Pub. 2019/0113501, each of which is incorporated herein by reference in its entirety and for any purpose. Any of the devices described may be utilized with the methods and apparatus described herein.

A portable or personal sampling unit may communicate with either a personal electronic device or a computer. Where the personal electronic device includes, but is not limited to a smartphone, cellular phone, or other personal transmitting device designed or programmed for receiving data from the personal sampling unit. Likewise, the computer is intended to include a personal computer, local server, remote server, etc. Data transmission from the personal sampling unit can occur to both or either the personal electronic device and/or the computer. Furthermore, synchronization between the personal electronic device and the computer is optional. Either the personal electronic device, the computer, and/or the personal sampling unit can transmit data to a remote server for data analysis as described herein. Alternatively, data analysis can occur, fully or partially, via a processor contained in a local device such as the sampling unit (or the computer or personal electronic device). In any case, the personal electronic device and/or computer can provide information to the individual, caretaker, or other individual.

The personal sampling unit receives a sample of exhaled air from the individual via a collection entry or opening. Hardware within the personal sampling unit may include any commercially available electrochemical gas sensor that detects CO gas within the breath sample, commercially available transmission hardware that transmits data (e.g., via Bluetooth®, cellular, or other radio waves to provide transmission of data). The transmitted data and associated measurements and quantification are then displayed on either (or both) a computer display or a personal electronic device. Alternatively, or in combination, any of the information can be selectively displayed on the portable sampling unit.

The electrochemical sensor contained within the sampling unit may typically have a response when exposed to a change in gas concentration such as when the user initially blows into the sampling unit. Prior to the user providing the eCO, the electrochemical sensor may remain at a nominal steady state voltage value depending upon the amount of ambient CO detected by the sensor within the unit. When exposed to a breath sample, the electrochemical sensor may display an initial transient response followed by a steady state response due to the change in gas concentration detected from the breath sample.

The steady state response component is indicative of the sensor sensitivity measured in, e.g., voltage per gas concentration (mV/ppm CO). Depending upon the sensitivity of the sensor given sensor degradation over time, this steady state response value may drift resulting in an increase or decrease of the voltage value. The transient response component is indicative of the stabilization speed of the sensor and again depending upon the sensitivity of the sensor, this transient response value may also drift but may increase or reduce the rate of voltage per gas concentration resulting in a flattened or steepened response curve.

It is possible to compensate for the transient response if the transient characteristics of the gas sensor are known. This may allow for an accurate prediction of the steady state response before the sensor has stabilized. In order to implement a correction to the sensor to account for degradation from its initial calibrated state, the drift in measurement over the transient response and the drift in the steady state response may be addressed independently of one another. The steady state response may be calibrated by exposing the sensor to a known gas concentration until a steady-state reading is obtained. Predicting the steady state response of the sensor in a breath sensor application may allow for the user to provide a relatively shorter duration breath. Generally, the sensor may be initially calibrated for both transient and steady state response at the time of manufacturing and the initially calibration values may be stored within the unit. The initial calibration may be determined in one variation by gathering data on sensor sensitivity over time in order to track the rate at which the sensitivity decreases. Based on this information, a linear or non-linear model which reflects the sensitivity drift over time may be developed and this model may be used to compensate for the sensitivity drift as a factor of time. For instance, if the sensor sensitivity were known to degrade by a certain percentage, e.g., 5% per year, a correction factor of the degradation percentage may be automatically applied by the processor, e.g., within the unit 20, to adjust the measured steady state values by 5% to account for sensor degradation.

During use by the user, the user may typically not have access to a CO source having a known concentration for steady state calibration purposes. Hence, the user may be instructed to perform a breath test where the user is instructed to hold their breath for, e.g., 10 or more seconds, to allow for the concentration of CO in the bloodstream to equalize with the concentration in the alveoli of their lungs. The gas in their mouth and trachea will likely be at a lower concentration of CO so as the user exhales into the sampling unit, the gas sensor may see a steadily increasing concentration of CO until the air in the mouth and trachea is exhausted, at which point the CO gas seen at the sensor approaches a constant concentration until the end of the breath. When the user stops exhaling, the CO gas concentration at the electrochemical sensor will return to the concentration in ambient air due to diffusion.

In some variations, during the breath test, the user may be instructed to inhale through the device after the initial exhalation into the device from holding their breath in order to bring the gas levels within the unit back to ambient. How quickly the concentration equalizes can be tailored by design aspects of the breath sensor unit such as volume of the device, flow path restrictions, sensor proximity to vent holes, how quickly the sensor consumes CO, etc. These values may be consistent within devices of the same model; however, it is also possible for the user to affect how quickly the gas concentration equalizes with ambient. For instance, the use could block vent holes to decrease equalization speed or to gently shake or inhale through the device in order to increase equalization speed.

Based upon the drop from the measured value of the near-constant CO concentration (near the end of the user's exhalation) back down to ambient, a transient time constant may be calculated characterizing the response of the measured drop and this calculated time constant value may be indicative of the degree of degradation of the sensor. The time constant may then be used to account for a corrected eCO measurement when the user exhales a breath sample into the unit for measurement.

With the various types of electrochemical sensors which may be utilized with the sampling unit, different sensor types may exhibit different modes of stability. Each of the various sensor stability modes are addressed in each of the following.

One type of sensor may have a sensor sensitivity which is stable in time but the stabilization speed may drift. During manufacture, the sensor may have both the sensitivity and stabilization speed calibrated by exposing the sensor to a step function change in gas concentration. The calibration parameters are stored on the device and used to calculate the CO level corresponding to the sensor's voltage output. The sensor within the sampling unit 20 may be provided to a user at which point the user may begin use by providing breath samples. The stabilization speed parameters may be periodically re-calibrated using the user's breath sampling. where the gas concentration at the end of a breath sample can be assumed to be steady state. When the user stops exhaling, the sensor may see a step response from the user's CO concentration to the carbon monoxide concentration in ambient air.

Another type of sensor may have a sensor sensitivity and stabilization speed which are both stable in time and minimal variability may exist within devices. During device development, the sensitivity and stabilization speed may be calculated by exposing the breath sensor to a step function change in gas concentration. Because there is no need to calibrate on a per-device basis, the sensitivity and stabilization speed parameters from the device development may be pre-loaded onto the device and the calibration parameters may also be stored onto the device and used to calculate the CO levels corresponding to the sensor's voltage output.

Yet another type of sensor may have a sensor sensitivity and stabilization speed which are both stable in time. During manufacturing, both the sensitivity and stabilization speed of the sensor may be calibrated by exposing the breath sensor to a step function change in gas concentration. The calibration parameters may be stored onto the device and used to calculate the CO levels corresponding to the sensor's voltage output. Alternatively, stabilization speed can be calibrated once using user breath sample.

Yet another type of sensor may have a sensor sensitivity which is provided in advance by a vendor but the stabilization speed may vary between devices. During manufacturing, sensitivity parameters may be programmed onto the device by using the value provided by the gas sensor manufacturer. The stabilization speed parameters may be initialized with an estimate obtained during device development and stabilization speed may be calibrated using the user's breath sample.

Yet another type of sensor may have a sensor sensitivity which is consistent within a manufacturing batch but stabilization speeds may vary between different devices. During manufacturing, the sensitivity parameters may be programmed onto the device by using the value provided by calibrating one or more sensors from the manufacturing batch. The stabilization speed parameters may be initialized using the value calculated by the calibration units, or with an estimate obtained during device development and stabilization speed may be calibrated using the user's breath sample.

Yet another type of sensor may have a sensor sensitivity and/or stabilization speed which varies over time in a consistent manner between devices. During manufacturing, the sensitivity and/or stabilization speed parameters may be programmed onto the sampling device along with a timestamp corresponding to the calibration date. The sensor drift model may also be loaded onto the device. Prior to using the calibration parameters to calculate a CO concentration from the sensor output, the parameters may be first adjusted by an aging factor based on the model. The aging factor may be applied for the sensor calibration prior to determining the sensor drift. Optionally, the sensor drift model may be updated and deployed to the user's sensor via a wireless option using any number of wireless protocols.

The aging factor may be applied in cases where the decrease in sensor response is known or can be experimentally verified. For instance, it may be generally assumed that sensor sensitivity may decrease between, e.g., 2-5% per year depending upon the storage conditions. In storage conditions typical for a warehouse environment, sensor sensitivity may be assumed to degrade by, e.g., 3% per year. As an example, for a device which was calibrated one year ago for which a 50 ppm CO level gave a 200 mV sensor response signal, a user providing a breath sample presently may generate a 100 mV response signal which correlates to a CO level of 25 ppm. However, due to sensor degradation over the past year, the 25 ppm value may be increased by the 3% offset (or by some other percentage) so that the CO level is increased to 25.75 ppm which may be rounded to 26 ppm.

The aging factor may be determined empirically by setting sufficient groups of devices at the different conditions, testing periodically, and then performing a multivariate regression analysis to determine the effect of each component (e.g., temperature, humidity, time). The two factors of temperature and humidity may be subdivided into ranges to provide a quick reference for determining the degradation rate. If a sufficient number of data points are available, a continuous distribution may be generated.

Yet another type of sensor may have a sensor sensitivity and/or stabilization speed which varies over time based upon environmental conditions. As described above, during manufacturing, the sensitivity and/or stabilization speed parameters may be programmed onto the sampling device along with a timestamp corresponding to the calibration date. The sensor drift model may also be loaded onto the device. In this variation, the sampling unit 20 may incorporate an environmental sensor package that can independently measure the parameters contained in the sensor drift model, e.g., temperature and relative humidity. The environmental sensor package may periodically measure these parameters and either instantaneously correct and update the calibration parameters and/or log and store the parameters for use in calculating the calibration parameters at the time of use.

Prior to using the calibration parameters for calculating the gas concentration from the sensor output, the parameters may be adjusted first by an aging factor, as previously described. Optionally, the sensor drift model may be updated and deployed to the user's sensor via a wireless update.

Another variation for calibrating the sensor may include having a sampling unit 20 which is configured to self-calibrate its transient sensor performance. While the sensor may be generally stable, the stabilization speed may be variable over time. Hence, a factory-calibration of sensitivity and stabilization speed may be combined with a periodic re-calibration of sensitivity speed based on heuristic models of clearing to improve sensor transient performance.

In one variation of the breath sensor apparatus, the apparatus may generally comprise a sampling unit having a housing configured to receive a sample breath from a user, a sensor positioned within the housing and in fluid communication with the sample breath when received within the housing, and a processor in electrical communication with the sensor. The processor may be configured to determine a dissipation time when the sensor is exposed to a near-constant concentration level of CO detected from the breath sample down to an ambient level of CO detected. The processor may also be configured to calculate a time constant based on the dissipation time and a reduction from the near-constant concentration level to the ambient level. Furthermore, the processor may also be configured to apply the time constant to a transient response of the sensor to account for drift in calibrating the sensor.

In one method for calibrating the sensor, the method may generally comprising receiving a breath sample from a user until the sensor detects a near-constant concentration level of CO from the breath sample, determining a length of time for the near-constant concentration level of CO to dissipate to an ambient level of CO, calculating a time constant based on the length of time and a reduction from the near-constant concentration level to the ambient level, and calibrating the sensor to account for drift by applying the time constant to a transient response of the sensor.

DETAILED DESCRIPTION OF THE INVENTION

In order increase the useful life of the breath sensor for detecting analytes such as CO from a user, various methods may be employed which increases the shelf life of the breath sampling device prior to being sold to the user and which also results in longer use by the user as well. This may not only increase the accuracy of the breath sensor but may also increase the ease-of-use of the sensor by providing a highly-accurate reading from breaths having relatively shorter exhalation durations than otherwise allowable.

In obtaining the eCO from the user, certain biometric data of the user may be obtained by non-invasively detecting and quantifying the smoking behavior for a user based on measuring one or more of the user's biometric data; however, other biometric data can also be used. Such measurements or data collection can use a portable measuring unit or a fixed measuring unit, either of which communicates with one or more electronic devices for performing the quantification analysis. Alternatively, the analysis can be performed in the portable/fixed unit. For example, the portable unit can be coupled to a keychain, to the individual's cigarette lighter, cell phone, or other item that will be with the individual on a regular basis. Alternatively, the portable unit can be a stand-alone unit or can be worn by the individual.

Figure 1A:
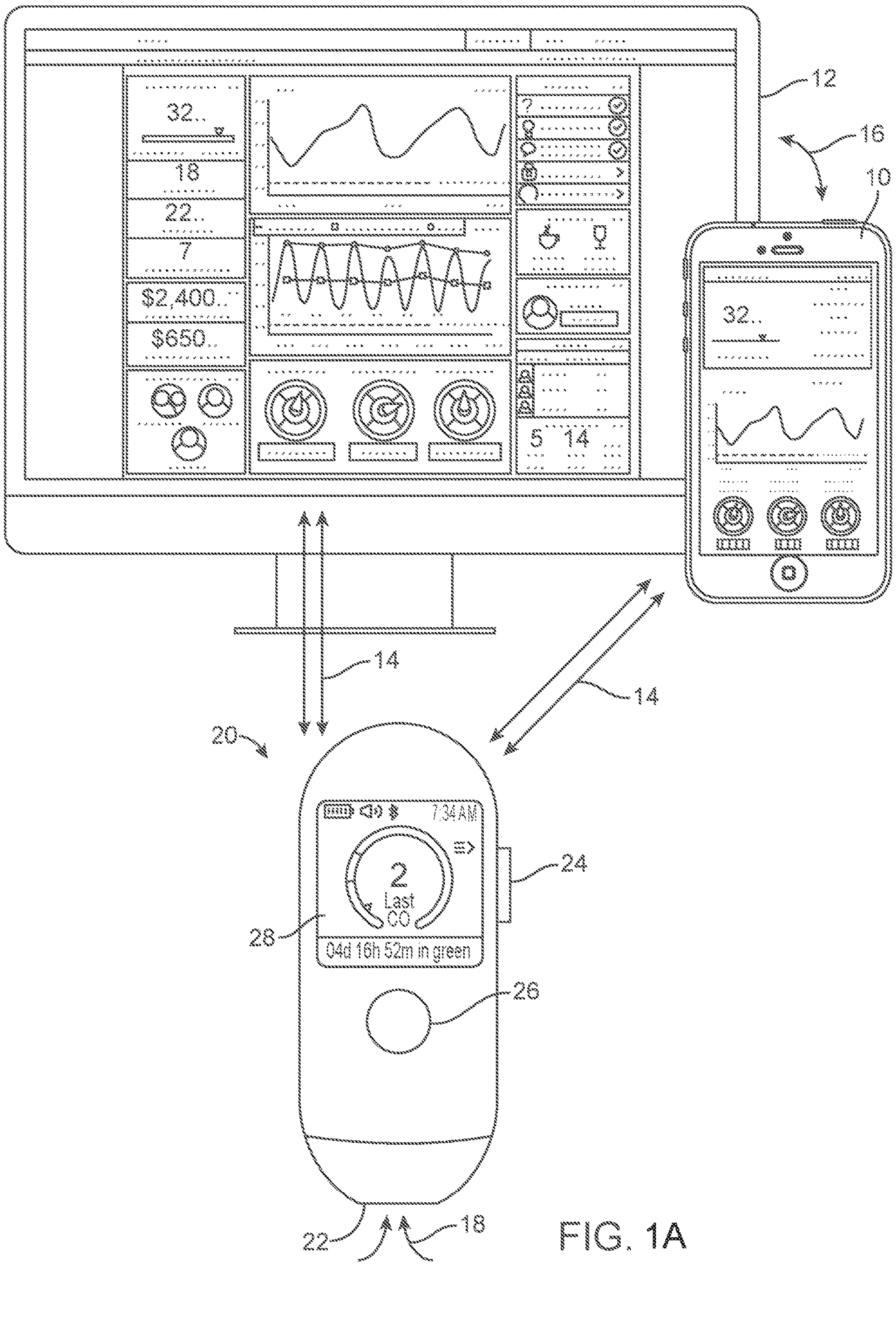
FIG. 1A illustrates a variation of a system which is able to receive the exhaled breath from a subject and detect various parameters and which can communicate with a one or more remote devices.

FIG. 1A illustrates one variation of a system and/or method in which a plurality of samples of biometric data are obtained from the user and analyzed to quantify the user's exposure to cigarette smoke such that the quantified information can be relayed to the individual, a medical caregiver, and/or other parties having a stake in the individual's health. The example discussed below employs a portable device 20 that obtains a plurality of samples of exhaled air from the individual with commonly available sensors that measure an amount of eCO within the sample of exhaled air. However, the quantification and information transfer are not limited to exposure of smoking based on exhaled air. As noted above, there are many sampling mechanisms to obtain a user's smoking exposure. The methods and devices described in the present example can be combined or supplemented with any number of different sampling mechanisms where possible while still remaining within the scope of the invention.

The measurement of eCO level has been known to serve as an immediate, non-invasive method of assessing a smoking status of an individual. The eCO levels for non-smokers can range between, e.g., 0 ppm to 6 ppm, or more particularly between, e.g., 3.61 ppm and 5.6 ppm.

As shown, a portable or personal sampling unit 20 may communicate with either a personal electronic device 10 or a computer 12. Where the personal electronic device 10 includes, but is not limited to a smartphone, cellular phone, or other personal transmitting device designed or programmed for receiving data from the personal sampling unit 20. Likewise, the computer 12 is intended to include a personal computer, local server, remote server, etc. Data transmission 14 from the personal sampling unit 20 can occur to both or either the personal electronic device 10 and/or the computer 12. Furthermore, synchronization 16 between the personal electronic device 10 and the computer 12 is optional. Either the personal electronic device 10, the computer 12, and/or the personal sampling unit 20 can transmit data to a remote server for data analysis as described herein. Alternatively, data analysis can occur, fully or partially, via a processor contained in a local device such as the sampling unit 20 (or the computer 12 or personal electronic device 10). In any case, the personal electronic device 10 and/or computer 12 can provide information to the individual, caretaker, or other individual as shown in FIG. 1A.

The personal sampling unit 20 receives a sample of exhaled air 18 from the individual via a collection entry or opening 22. Hardware within the personal sampling unit 20 may include any commercially available electrochemical gas sensor that detects CO gas within the breath sample, commercially available transmission hardware that transmits data 14 (e.g., via Bluetooth®, cellular, or other radio waves to provide transmission of data). The transmitted data and associated measurements and quantification are then displayed on either (or both) a computer display 12 or a personal electronic device 10. Alternatively, or in combination, any of the information can be selectively displayed on the portable sampling unit 20.

The personal sampling unit 20 (or personal breathing unit) can also employ standard ports to allow direct-wired communication with the respective devices 10 and 12. In certain variations, the personal sampling unit 20 can also include memory storage, either detachable or built-in, such that the memory permits recording of data and separate transmission of data. Alternatively, the personal sampling unit can allow simultaneous storage and transmission of data. Additional variations of the device 20 do not require memory storage. In addition, the unit 20 can employ any number of GPS components, inertial sensors (to track movement), and/or other sensors that provide additional information regarding the patient's behavior.

The personal sampling unit 20 can also include any number of input trigger (such as a switch or sensors) 24, 26. As described below, the input trigger 24, 26 may allow the individual to prime the device 20 for delivery of a breath sample 18 or to record other information regarding the cigarette such as quantity of cigarette smoked, the intensity, etc. In addition, variations of the personal sampling unit 20 may also associate a timestamp of any inputs to the device 20. For example, the personal sampling unit 20 can associate the time at which the sample is provided and provide the measured or inputted data along with the time of the measurement when transmitting data 14. Alternatively, the personal sampling device 20 can use alternate mechanisms to identify the time that the sample is obtained. For example, given a series of samples rather than recording a timestamp for each sample, the time periods between each of the samples in the series can be recorded. Therefore, identification of a timestamp of any one sample allows determination of the time stamp for each of the samples in the series.

In certain variations, the personal sampling unit 20 may be designed such that it has a minimal profile and can be easily carried by the individual with minimal effort. Therefore the input triggers 24 can comprise low profile tactile switches, optical switches, capacitive touch switches, or any commonly used switch or sensor. The portable sampling unit 20 can also provide feedback or information to the user using any number of commonly known techniques. For example, as shown, the portable sampling unit 20 can include a screen 28 that shows select information as discussed below. Alternatively or additionally, the feedback can be in the form of a vibrational element, an audible element, and a visual element (e.g., an illumination source of one or more colors). Any of the feedback components can be configured to provide an alarm to the individual, which can serve as a reminder to provide a sample and/or to provide feedback related to the measurement of smoking behavior. In addition, the feedback components can provide an alert to the individual on a repeating basis in an effort to remind the individual to provide periodic samples of exhaled air to extend the period of time for which the system captures biometric (such as eCO, CO levels, $H_2$ etc.) and other behavioral data (such as location either entered manually or via a GPS component coupled to the unit, number of cigarettes, or other triggers). In certain cases, the reminders can be triggered at higher frequency during the initial program or data capture. Once sufficient data is obtained, the reminder frequency can be reduced.

In obtaining the breath sample with the sampling unit 20, instructions may be provided on the personal electronic device 10 or computer display 12 for display to the subject in a guided breath test for training the subject to use the unit 20. Generally, the subject may be instructed, e.g., on the screen 28 of the electronic device 10, to first inhale away from the unit 20 and then to exhale into the unit 20 for a set period of time. The unit 20 may optionally incorporate one or more pressure sensors fluidly coupled with, e.g., check valves, to detect if the subject inhales through the unit 20.

Figure 1B:
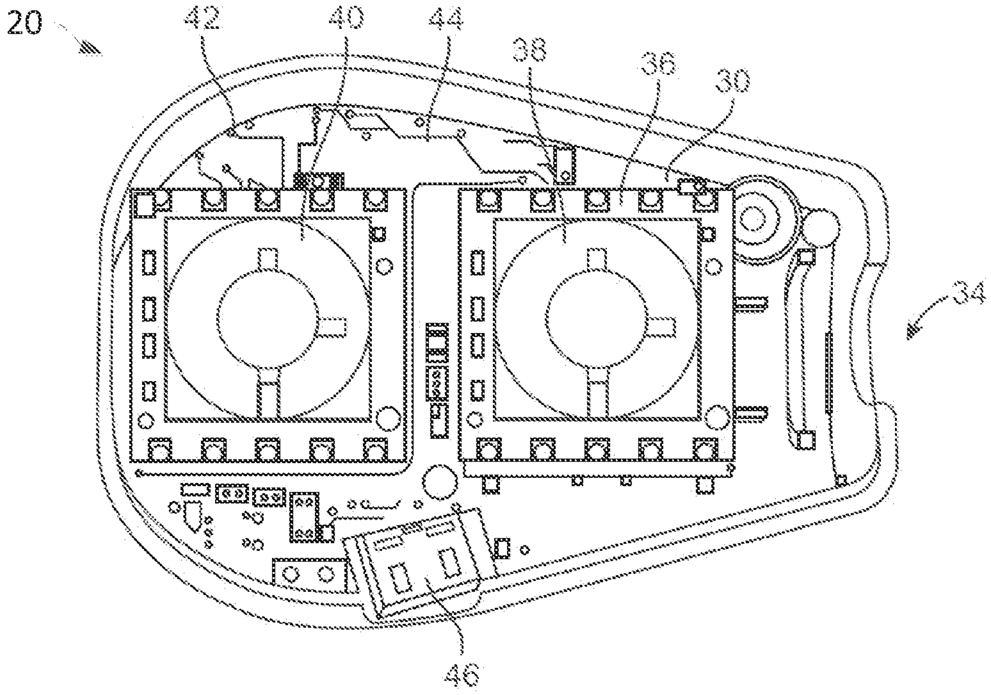
FIG. 1B illustrates one variation of the internal circuitry and sensors contained within the housing of the breath sensor.

FIG. 1B shows the sampling unit 20 with a portion of the housing 30 and collection entry or opening 22 removed to show a top view of the electrochemical sensors contained within. In this variation, a first sensor 38 and second sensor 42 (either or both of the sensors 38, 42 may include CO and $H_2$ sensors) are shown optionally positioned upon respect respective sensor platforms 36, 40 which in turn may be mounted upon a substrate such as a printed circuit board 44. Although in other variations, one or more sensors may be used depending upon the parameters being detected. In other variations, the one or more sensors may be mounted directly upon the printed circuit board 44. A power port and/or data access port 46 may also be seen integrated with the printed circuit board 44 and readily accessible by a remote device such as a computer, server, smartphone, or other device. As shown, multiple sensors 38, 42 or a single sensor may be used to detect the parameters from the sampled breath.

In other variations, at least one CO sensor or multiple CO sensors may be implemented alone. Alternatively, one or more CO sensors may be used along with one or more $H_2$ sensors in combination. If both a CO and $H_2$ sensor are used, the readings from the $H_2$ sensor may be used to account for or compensate for any $H_2$ signals detected by the CO sensor since many CO sensors have a cross-sensitivity to $H_2$ which is frequently present in sufficient quantity to potentially affect CO measurement in the breath of people. If a CO sensor is used without an $H_2$ sensor, various methods may be applied to reduce any $H_2$ measurement interference to a nominally acceptable level. However, the use of an $H_2$ sensor to directly measure and compensate for the presence of $H_2$ may facilitate CO measurement. The sensors may also include any number of different sensor types including chemical gas sensors, electrochemical gas sensors, etc. for detecting agents such as carbon monoxide in the case of detecting smoking related inhalation.

Further examples of breath sampling devices and methods for determining and quantifying eCO levels from a user are described in further detail in various patents, e.g., U.S. Pat. Nos. 9,861,126; 10,206,572; 10,306,922; 10,335,032, and U.S. Pat. Pub. 2019/0113501, each of which is incorporated herein by reference in its entirety and for any purpose. Any of the devices described may be utilized with the methods and apparatus described herein.

Figure 2:
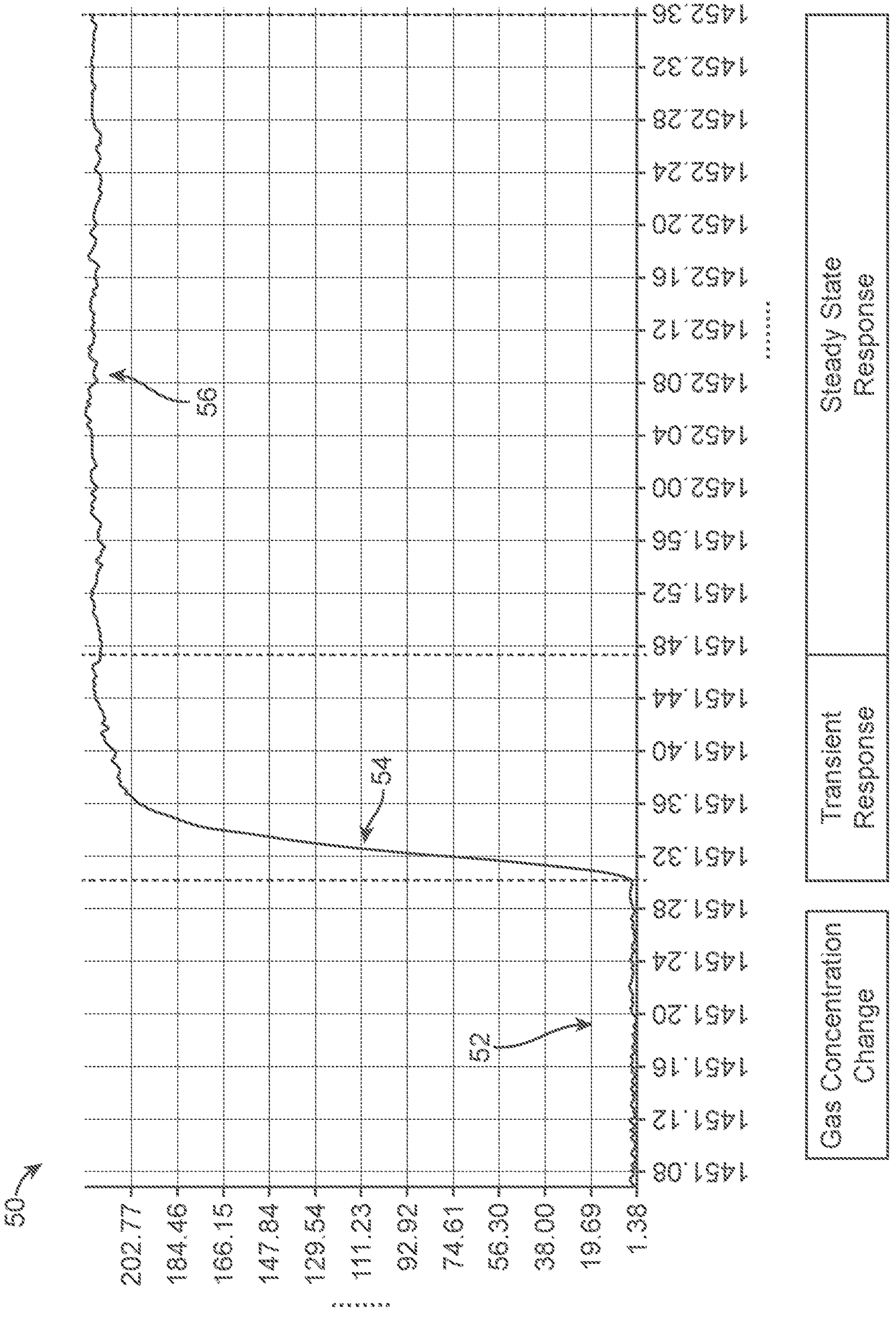
FIG. 2 illustrates an example of the voltage response of an electrochemical sensor over time having a transient response and a stead state response.

The electrochemical sensor contained within the sampling unit 20 may typically have a response when exposed to a change in gas concentration such as when the user initially blows into the sampling unit 20. Prior to the user providing the eCO, the electrochemical sensor may remain at a nominal steady state voltage value 52 depending upon the amount of ambient CO detected by the sensor within the unit 20, as shown in the exemplary graph 50 of FIG. 2 which illustrates the voltage response of the electrochemical sensor over time. When exposed to a breath sample, the electrochemical sensor may display an initial transient response 54 followed by a steady state response 56, as illustrated, due to the change in gas concentration detected from the breath sample.

The steady state response component 56 is indicative of the sensor sensitivity measured in, e.g., voltage per gas concentration (mV/ppm CO). Depending upon the sensitivity of the sensor given sensor degradation over time, this steady state response value may drift resulting in an increase or decrease of the voltage value (e.g., displacement of the steady state response vertically along the graph 50). The transient response component 54 is indicative of the stabilization speed of the sensor and again depending upon the sensitivity of the sensor, this transient response value may also drift but may increase or reduce the rate of voltage per gas concentration resulting in a flattened or steepened response curve (e.g., shrinkage or expansion of the transient response horizontally along the graph 50).

Figure 3A:
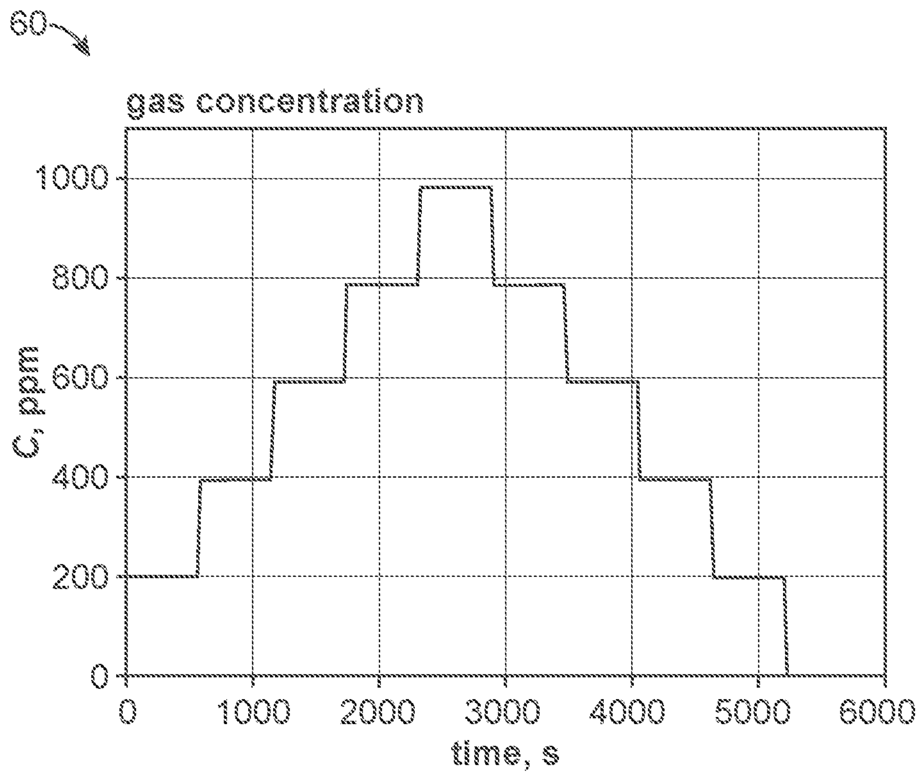
FIGS. 3A and 3B illustrate an example for how the sensor may be effectively compensated for degradation by utilizing a dynamic correction algorithm.
Figure 3B:
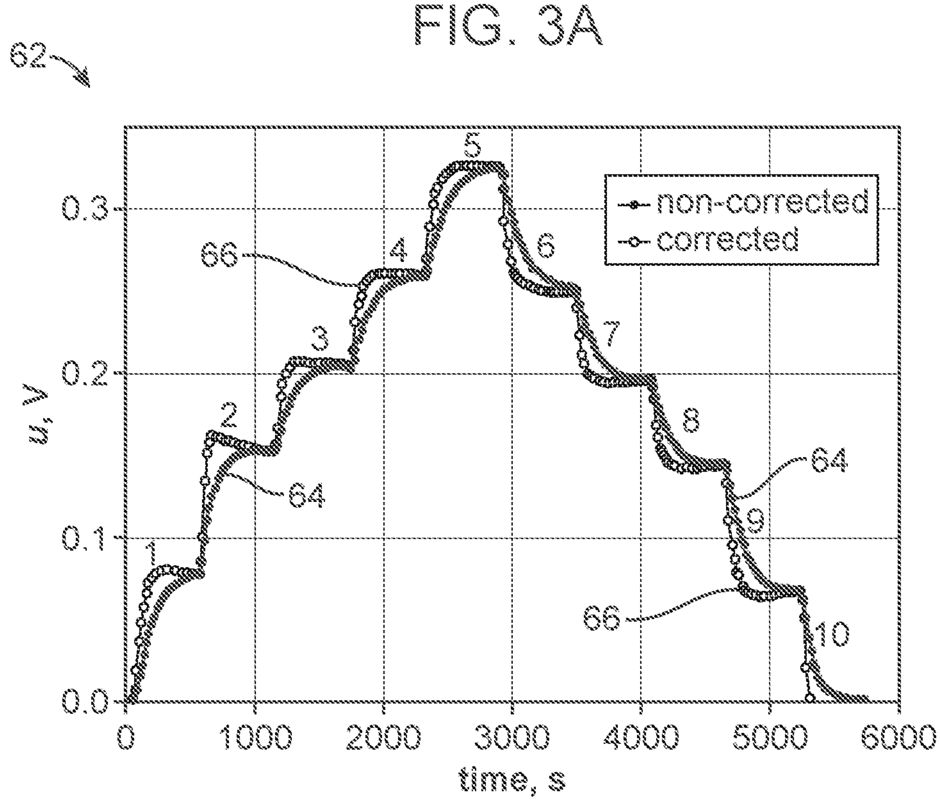

It is possible to compensate for the transient response 54 if the transient characteristics of the gas sensor are known. This may allow for an accurate prediction of the steady state response 56 before the sensor has stabilized. FIGS. 3A and 3B illustrate an example for how the sensor may be effectively compensated for degradation by utilizing a dynamic correction algorithm. FIG. 3A shows a graph 60 illustrating an example of a gas being provided at varying levels of concentration C (ppm) over time for measurement purposes. FIG. 3B shows a graph 62 illustrating the resulting measurements via an electrochemical sensor corresponding to the varying concentration levels of the gas from FIG. 3A. The curves 64 show the corresponding non-corrected voltage obtained from the sensor while curves 66 shows the corresponding corrected voltage obtained from the sensor with a correction resulting in a relatively more accurate voltage reading corresponding to the actual gas concentration values.

In order to implement a correction to the sensor to account for degradation from its initial calibrated state, the drift in measurement over the transient response 54 and the drift in the steady state response 56 may be addressed independently of one another. The steady state response 56 may be calibrated by exposing the sensor to a known gas concentration until a steady-state reading is obtained. Predicting the steady state response of the sensor in a breath sensor application may allow for the user to provide a relatively shorter duration breath. Generally, the sensor may be initially calibrated for both transient and steady state response at the time of manufacturing and the initially calibration values may be stored within the unit 20. The initial calibration may be determined in one variation by gathering data on sensor sensitivity over time in order to track the rate at which the sensitivity decreases. Based on this information, a linear or non-linear model which reflects the sensitivity drift over time may be developed and this model may be used to compensate for the sensitivity drift as a factor of time. For instance, if the sensor sensitivity were known to degrade by a certain percentage, e.g., 5% per year, a correction factor of the degradation percentage may be automatically applied by the processor, e.g., within the unit 20, to adjust the measured steady state values by 5% to account for sensor degradation.

The transient response may be calibrated by exposing the sensor to a known change in gas concentration, and parameters in a model that converts the sensor voltage output may be fit to the shape of the gas concentration curve as illustrated in the corrected curves 66 shown between FIGS. 3A and 3B. The shape of the concentration versus time curve needs to be known in advance (e.g., a step response from one concentration to another); however, the gas concentration values do not need to be known because this model may fit against the steady state response, which is calibrated separately.

During use by the user, the user may typically not have access to a CO source having a known concentration for steady state calibration purposes. Hence, the user may be instructed to perform a breath test where the user is instructed to hold their breath for, e.g., 10 or more seconds, to allow for the concentration of CO in the bloodstream to equalize with the concentration in the alveoli of their lungs. The gas in their mouth and trachea will likely be at a lower concentration of CO so as the user exhales into the sampling unit 20, the gas sensor may see a steadily increasing concentration of CO until the air in the mouth and trachea is exhausted, at which point the CO gas seen at the sensor approaches a constant or near-constant concentration until the end of the breath. When the user stops exhaling, the CO gas concentration at the electrochemical sensor will return to the concentration in ambient air due to diffusion.

Figure 4:
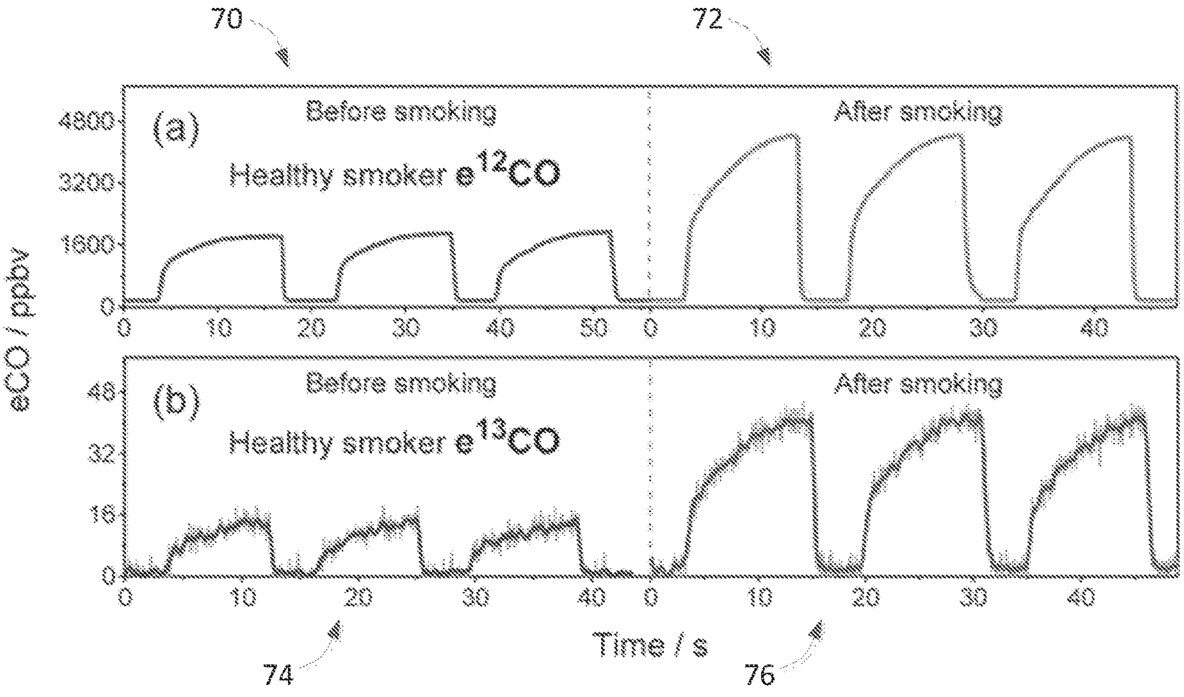
FIG. 4 shows an example of the measured eCO and eCO expirograms from a sample breath of a healthy occasional smoker before smoking and after smoking.

FIG. 4 shows an example of the measured eCO and eCO expirograms from a sample breath of a healthy occasional smoker before smoking (19 hours after their last cigarette) in eCO graph 70 and the eCO graph 72 obtained 15 sec after smoking. The corresponding eCO expirogram 74 shows the values corresponding to eCO graph 70 and eCO expirogram 76 shows the values corresponding to eCO graph 72 to illustrate how the measured eCO values begin to reach a steady state after a period of time from when the user has started exhalation and drops back to ambient levels in a transient response.

In some variations, during the breath test described above, the user may be instructed to inhale through the device after the initial exhalation into the device from holding their breath in order to bring the gas levels within the unit 20 back to ambient. How quickly the concentration equalizes can be tailored by design aspects of the breath sensor unit 20 such as volume of the device, flow path restrictions, sensor proximity to vent holes, how quickly the sensor consumes CO, etc. These values may be consistent within devices of the same model; however, it is also possible for the user to affect how quickly the gas concentration equalizes with ambient. For instance, the use could block vent holes to decrease equalization speed or to gently shake or inhale through the device in order to increase equalization speed.

Based upon the drop from the measured value of the near-constant CO concentration (near the end of the user's exhalation) back down to ambient, a transient time constant may be calculated characterizing the response of the measured drop and this calculated time constant value may be indicative of the degree of degradation of the sensor. The time constant may then be used to account for a corrected eCO measurement when the user exhales a breath sample into the unit 20 for measurement.

Figure 5:
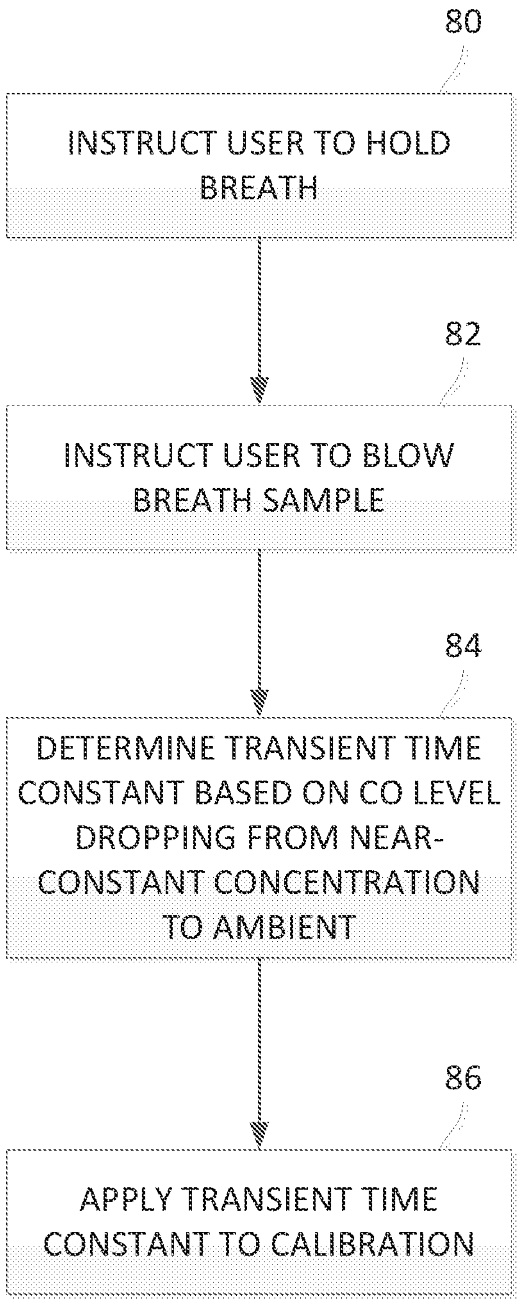
FIG. 5 illustrates a flow diagram showing how a time constant may be calculated for calibrating the sensor.

FIG. 5 illustrates a flow diagram showing how a time constant may be calculated for calibrating the sensor, as described above. The user may be initially instructed 80 (e.g., via the sampling unit 20) to hold their breath for, e.g., 10 or more seconds, to allow for the concentration of CO in the bloodstream to equalize with the concentration in the alveoli of their lungs. The user may then be instructed 82 to blow a breath sample into the device to allow for the concentration of CO in the sample to approach a constant concentration until the end of the breath. When the user stops exhaling, the CO gas concentration at the electrochemical sensor will return to the concentration in ambient air due to diffusion or the user may be further instructed to facilitate the diffusion of CO within the device back to ambient. In either case, the transient time constant based on the drop from the near-constant CO concentration back to ambient may be determined 84. The time constant may then be used to calibrate the sensor 86 to account for a corrected eCO measurement when the user exhales a breath sample into the unit 20 for measurement.

Because it is possible for the user to affect the response speed, as described (e.g., covering vent holes to reduce gas diffusion speed, shaking the sensor to increase diffusion speed, etc.), several transient response times may be stored for evaluation and the stored response times may be evaluated according to certain criteria. For instance, the current calibration value for response speed may be used in a model for minimum response speed assuming a step response in gas concentration from the user's breath concentration to the concentration in ambient air. If the lowest response speed in the stored data is below the value created by the model, the calibration parameter may be decreased to the lowest value in the stored data.

Another criteria for evaluation may include the use of the current calibration value for response speed in a model for maximum response speed assuming that all the sensor vent holes are blocked. If the highest response speed in the stored data is above the value created by the model, the calibration parameter may be changed to the highest value in the stored data.

Yet another criteria for evaluation may also include the creation of models for each combination of user actions that might affect concentration equalization speed. If any models have a distinctive waveform that matches the concentration equalization waveform, the calibration parameter may be updated according to that model.

Yet another criteria for evaluation may also include increasing of the calibration value slightly if all the responses in the stored data are higher than the calibration value.

For assigning the initial sensitivity, including batch testing which may not allow evaluation of an initial transient response speed parameter. In the case of such batch testing, a population-level default transient response speed parameter may be determined by pre-production and ongoing testing, and then this parameter may be updated over time.

MODES OF SENSOR STABILITY

With the various types of electrochemical sensors which may be utilized with the sampling unit 20, different sensor types may exhibit different modes of stability. Each of the various sensor stability modes are addressed in each of the following.

Case 1

This type of sensor may have a sensor sensitivity which is stable in time but the stabilization speed may drift. During manufacture, the sensor may have both the sensitivity and stabilization speed calibrated by exposing the sensor to a step function change in gas concentration. The calibration parameters are stored on the device and used to calculate the CO level corresponding to the sensor's voltage output. The sensor within the sampling unit 20 may be provided to a user at which point the user may begin use by providing breath samples. The stabilization speed parameters may be periodically re-calibrated using the user's breath sampling. where the gas concentration at the end of a breath sample can be assumed to be steady state. When the user stops exhaling, the sensor may see a step response from the user's CO concentration to the carbon monoxide concentration in ambient air.

Case 2

This type of sensor may have a sensor sensitivity and stabilization speed which are both stable in time and minimal variability may exist within devices. During device development, the sensitivity and stabilization speed may be calculated by exposing the breath sensor to a step function change in gas concentration. Because there is no need to calibrate on a per-device basis, the sensitivity and stabilization speed parameters from the device development may be pre-loaded onto the device and the calibration parameters may also be stored onto the device and used to calculate the CO levels corresponding to the sensor's voltage output.

Case 3

This type of sensor may have a sensor sensitivity and stabilization speed which are both stable in time. During manufacturing, both the sensitivity and stabilization speed of the sensor may be calibrated by exposing the breath sensor to a step function change in gas concentration. The calibration parameters may be stored onto the device and used to calculate the CO levels corresponding to the sensor's voltage output. Alternatively, stabilization speed can be calibrated once using user breath sample.

Case 4

This type of sensor may have a sensor sensitivity which is provided in advance by a vendor but the stabilization speed may vary between devices. During manufacturing, sensitivity parameters may be programmed onto the device by using the value provided by the gas sensor manufacturer. The stabilization speed parameters may be initialized with an estimate obtained during device development and stabilization speed may be calibrated using the user's breath sample.

Case 5

This type of sensor may have a sensor sensitivity which is consistent within a manufacturing batch but stabilization speeds may vary between different devices. During manufacturing, the sensitivity parameters may be programmed onto the device by using the value provided by calibrating one or more sensors from the manufacturing batch. The stabilization speed parameters may be initialized using the value calculated by the calibration units, or with an estimate obtained during device development and stabilization speed may be calibrated using the user's breath sample.

Case 6

Figure 6:
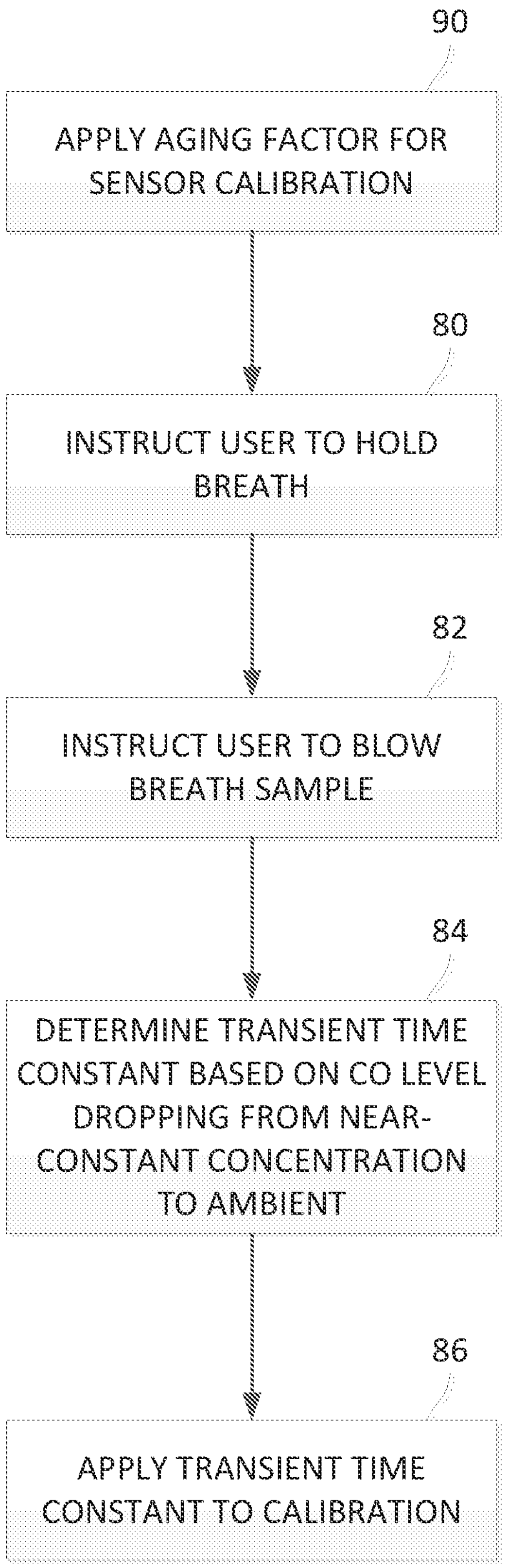
FIG. 6 illustrates a flow diagram showing how an aging factor may be applied for calibration prior to a time constant calculation for calibrating the sensor.

This type of sensor may have a sensor sensitivity and/or stabilization speed which varies over time in a consistent manner between devices. During manufacturing, the sensitivity and/or stabilization speed parameters may be programmed onto the sampling device along with a timestamp corresponding to the calibration date. The sensor drift model may also be loaded onto the device. Prior to using the calibration parameters to calculate a CO concentration from the sensor output, the parameters may be first adjusted by an aging factor based on the model described in case 1 above and as illustrated in FIG. 6. The aging factor may be applied for the sensor calibration 90 as shown prior to determining the sensor drift, as described above. Optionally, the sensor drift model may be updated and deployed to the user's sensor via a wireless option using any number of wireless protocols.

The aging factor may be applied in cases where the decrease in sensor response is known or can be experimentally verified. For instance, it may be generally assumed that sensor sensitivity may decrease between, e.g., 2-5% per year depending upon the storage conditions. In storage conditions typical for a warehouse environment, sensor sensitivity may be assumed to degrade by, e.g., 3% per year. As an example, for a device which was calibrated one year ago for which a 50 ppm CO level gave a 200 mV sensor response signal, a user providing a breath sample presently may generate a 100 mV response signal which correlates to a CO level of 25 ppm. However, due to sensor degradation over the past year, the 25 ppm value may be increased by the 3% offset (or by some other percentage) so that the CO level is increased to 25.75 ppm which may be rounded to 26 ppm.

The aging factor may be determined empirically by setting sufficient groups of devices at the different conditions, testing periodically, and then performing a multivariate regression analysis to determine the effect of each component (e.g., temperature, humidity, time). The two factors of temperature and humidity may be subdivided into ranges to provide a quick reference for determining the degradation rate. For instance, the following table shows an example of the resulting sensor degradation rate for a given temperature range and relative humidity range:

TABLE 1

Sensor degradation over temperature and relative humidity (RH).

| TEMPERATURE | 15-35% RH | 35-85% RH |
|---|---|---|
| 12°-26° C. | 4% per year | 2% per year |
| 26°-40° C. | 8% per year | 3% per year |

Generally, the lower the storage temperature (e.g., ≤26° C.) and lower relative humidity (e.g., ≤35% RH) results in a relatively higher degradation rate while a lower storage temperature (e.g., ≤26° C.) and higher relative humidity (e.g., ≥35% RH) results in a relatively lower degradation rate. Likewise, the higher the storage temperature (e.g., ≥26° C.) and lower relative humidity (e.g., ≤35% RH) results in a relatively higher degradation rate while a higher storage temperature (e.g., ≥26° C.) and higher relative humidity (e.g., ≥35% RH) results in a relatively lower degradation rate. However, because the effects of temperature and humidity can be separated from one another, the effects may also be generalized in that a relatively higher storage temperature may result in a relatively higher degradation rate and a relatively lower storage temperature may result in a relatively lower degradation rate. Likewise, a relatively lower relative humidity may result in a relatively higher degradation rate and a relatively higher relative humidity may result in a relatively lower degradation rate. If a sufficient number of data points are available, a continuous distribution may be generated.

Case 7

This type of sensor may have a sensor sensitivity and/or stabilization speed which varies over time based upon environmental conditions. As described above, during manufacturing, the sensitivity and/or stabilization speed parameters may be programmed onto the sampling device along with a timestamp corresponding to the calibration date. The sensor drift model may also be loaded onto the device. In this variation, the sampling unit 20 may incorporate an environmental sensor package that can independently measure the parameters contained in the sensor drift model, e.g., temperature and relative humidity. The environmental sensor package may periodically measure these parameters and either instantaneously correct and update the calibration parameters and/or log and store the parameters for use in calculating the calibration parameters at the time of use.

Prior to using the calibration parameters for calculating the gas concentration from the sensor output, the parameters may be adjusted first by an aging factor, as previously described. Optionally, the sensor drift model may be updated and deployed to the user's sensor via a wireless update.

Self-Calibration

Another variation for calibrating the sensor may include having a sampling unit 20 which is configured to self-calibrate its transient sensor performance. While the sensor may be generally stable, the stabilization speed may be variable over time. Hence, a factory-calibration of sensitivity and stabilization speed may be combined with a periodic re-calibration of sensitivity speed based on heuristic models of clearing to improve sensor transient performance.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A breath sensor apparatus, comprising:

a sampling unit having a housing configured to receive a sample breath from a user;

an electrochemical sensor positioned within the housing and in fluid communication with the sample breath when received within the housing;

a processor in electrical communication with the electrochemical sensor such that the processor is configured to receive a measurement from the electrochemical sensor corresponding to a level of carbon monoxide sensed in the sample breath, wherein the processor is configured to apply an aging factor to the measurement based upon a length of time passing from an initial calibration of the sensor to account for a degradation rate of the sensor over the length of time, wherein the aging factor adjusts the measurement to account for the degradation rate, and wherein the processor is further configured to apply a re-calibration to the electrochemical sensor to adjust for a stabilization speed of the measurement, wherein the re-calibration comprises adjusting initial parameters obtained from an initial calibration based on a transient response component collected after the sample breath.

2. The apparatus of claim 1 wherein the processor is configured to apply the aging factor by adding the aging factor of an offset value of a calibrated measurement to the measurement for each length of time of a year.

3. The apparatus of claim 1 wherein the processor is configured to modify the aging factor based upon a temperature level and a humidity level to which the sensor is exposed over the length of time.

4. The apparatus of claim 3 wherein storage temperature which is relatively lower than a predetermined storage temperature corresponds to a degradation rate which is relatively lower than a predetermined degradation rate based on the predetermined storage temperature.

5. The apparatus of claim 3 wherein a storage temperature which is relatively higher than a predetermined storage temperature corresponds to a degradation rate which is relatively higher than a predetermined degradation rate based on the predetermined storage temperature.

6. The apparatus of claim 3 wherein a relative humidity which is relatively lower than a predetermined storage humidity corresponds to a degradation rate which is relatively higher than a predetermined degradation rate based on the predetermined storage humidity.

7. The apparatus of claim 3 wherein a relative humidity which is relatively higher than a predetermined storage humidity corresponds to a degradation rate which is relatively lower than a predetermined degradation rate based on the predetermined storage humidity.

8. The apparatus of claim 1 wherein the processor is further configured to modify the aging factor based upon one or more environmental factors to which the sensor is exposed over the length of time.

* * * * *